United States Patent [19]

Tojo

[11] Patent Number: 4,753,224
[45] Date of Patent: Jun. 28, 1988

[54] ENDOSCOPE TIP

[75] Inventor: Yoshikazu Tojo, Hachioji, Japan

[73] Assignee: Olympus Optical Co., Ltd., Tokyo, Japan

[21] Appl. No.: 53,887

[22] Filed: May 20, 1987

[30] Foreign Application Priority Data

May 21, 1986 [JP] Japan ................................. 61-116793

[51] Int. Cl.$^4$ ............................................. G02B 23/26
[52] U.S. Cl. ...................................... 128/6; 73/865.8;
350/96.26; 356/241
[58] Field of Search ............................ 128/4, 5, 6, 7;
73/865.8; 350/96.26; 356/241

[56] References Cited

U.S. PATENT DOCUMENTS

| 3,799,150 | 3/1974 | Bonnet | 128/6 |
| 4,530,568 | 7/1985 | Haduch et al. | 350/96.26 |
| 4,576,147 | 3/1986 | Hashiguchi | 128/6 |

Primary Examiner—William H. Grieb
Attorney, Agent, or Firm—Armstrong, Nikaido, Marmelstein & Kubovcik

[57] ABSTRACT

In an endoscope having an objective optical system and an illuminating optical system formed in the tip of the insertable part; an incised or inclined surface is formed on the periphery of the tip by incising or cutting away the outer surface of the tip to provide a surface which is not parallel with the longitudinal axis of the insertable part but is closely adjacent to the objective optical system.

10 Claims, 8 Drawing Sheets

ENDOSCOPE TIP

BACKGROUND OF THE INVENTION

This invention relates to an endoscope tip useful for viewing and inspecting relatively inaccessible objects. More specifically, the invention is particularly useful in an industrial endoscope used to inspect weld joints provided interiorly of piping and in jet engine combustion chambers.

Figure 1:
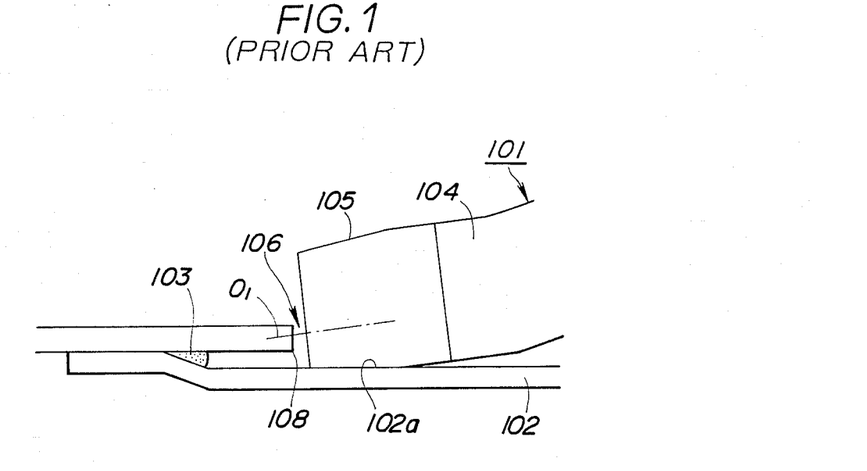
FIG. 1 is an elarged view showing the tip of a prior art endoscope in use.
Figure 2:
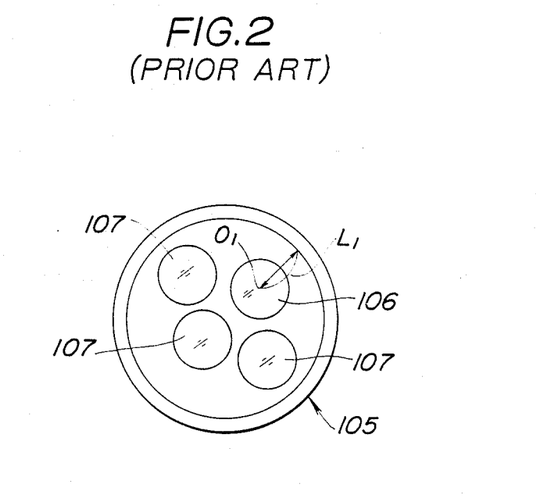
FIG. 2 is an end view of the endoscope tip of FIG. 1.

FIG. 1 shows an endoscope 101 having a conventional or prior art tip 105 located internally of a jet engine in position to inspect a weldment 103 provided between a projecting edge 108 of one part and a liner 102. FIG. 2 shows an end view of the prior art tip 105 which is provided with an observing window 106 and three illuminating windows 107.

The center $0_1$ of the observing window 106 is separated by a distance $L_1$ from the periphery of the tip 105. The center $0_1$ represents the axis of the objective lens system located in the tip 105 behind the observing window 106 and, as illustrated by FIG. 1, there are instances where the distance $L_1$ is too great to permit adequate viewing or illumination of an object to be inspected. For example, in FIG. 1 the projecting edge part 108 intercepts the axis $0_1$ of the objective lens system thereby disrupting the visual field and preventing an adequate image of the weldment 103 for inspection purposes. The amount of light available to illuminate the weldment 103 may also be localized or totally inadequate since the illuminating windows 107 are rotated out of the limited field of vision as the observing window 106 is positioned closely adjacent the inner surface 102a of the liner 102.

SUMMARY OF THE INVENTION

An object of this invention is to provide a tip for an endoscope which will permit observation of a welded part of a liner or the like from an angle closely adjacent to a wall surface.

Another object of this invention is to provide an improved endoscope tip which can be easily formed and which will permit observation to be made from a low angle of incidence adjacent to a wall surface.

According to the present invention, an endoscope having an observing objective optical system arranged at the end of the tip of the insertable part is provided with a tip incised or at least partly cut away on the outer surface to form an incised, tapered or inclined surface adjacent to the objective optical system so an observation may be made from a position very close to a wall surface by placing the incised or tapered surface in contact with the wall surface.

DETAILED DESCRIPTION OF THE PREFERRED EMBODIMENTS

Figure 3:
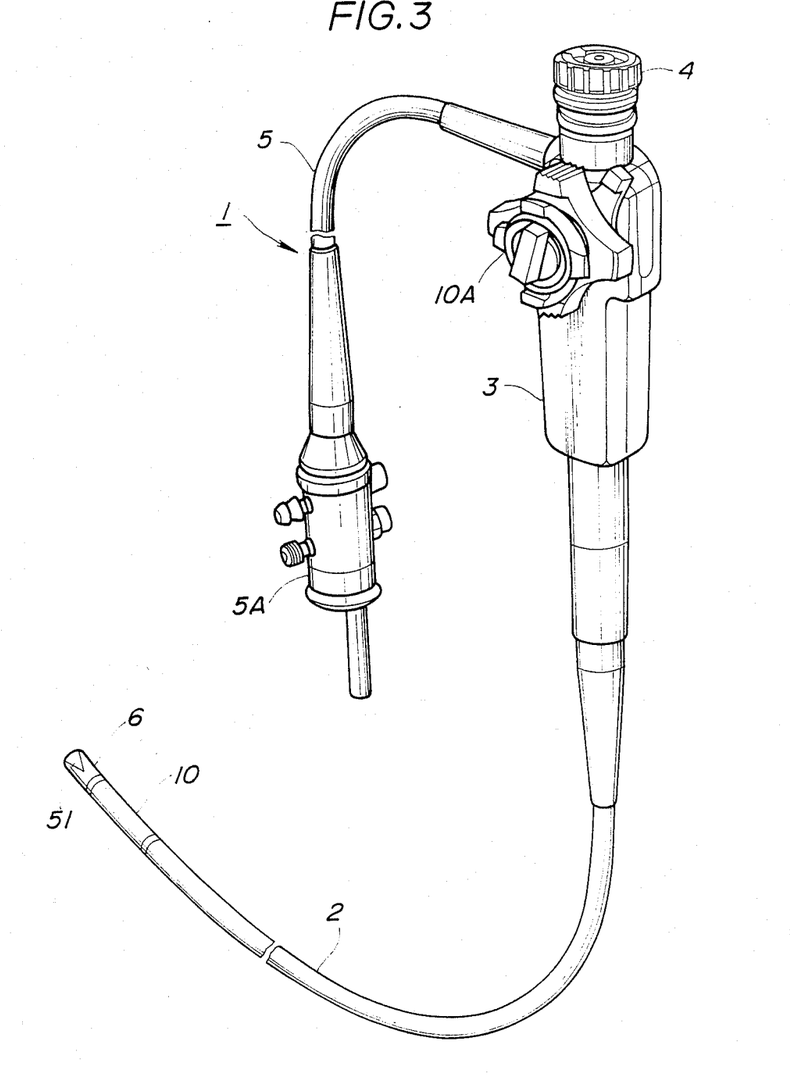
FIG. 3 is a perspective view of an endoscope incorporating one embodiment of the invention.

FIGS. 3-12 illustrate a first embodiment of the invention. FIG. 3 shows an industrial endoscope 1 having an elongate flexible tubular element or part 2 and an illuminating light transmitting guide cable 5 both of which are connected to a larger operating or control unit 3. The elongate, flexible tubular element 2 is insertable into a pipe cavity or the like and an eyepiece 4 connected to the rear end of the control unit 3 enables the operator to view remote objects adjacent the endoscope tip 6 in a pipe cavity or other relatively inaccessible location.

The elongate, flexible tubular element 2 contains within its tip 6 an objective lens system 7 (shown in FIGS. 5 and 6) for imaging an object so that an optical image formed by the lens system 7 may be transmitted through an image guide 8 comprising a plurality of optical fibers to the control unit 3 where the image is magnified and may be observed through the eyepiece 4. Three light guides 9, each of which also comprises a plurality of optical fibers are also provided internally of the tubular element 2. Each of the light guides 9 transmits light from a source, not shown in the drawings but associated with the connector 5A, to its respective illuminating or light distributing lens 44 fixed at the end of endoscope tip 6. Light transmitted by the three light guides 9 is distributed and projected by the lenses 44 to illuminate objects adjacent the endoscope 6 which are to be imaged and viewed through the above mentioned object lens system.

A portion of the tubular element 2 formed adjacent to the tip 6 and designated by the reference numeral 10 is specially constructed to permit remote controlled movement, both horizontally and vertically, of the tip 6 by actuation of knob 10A provided on the control unit 3.

Figure 6:
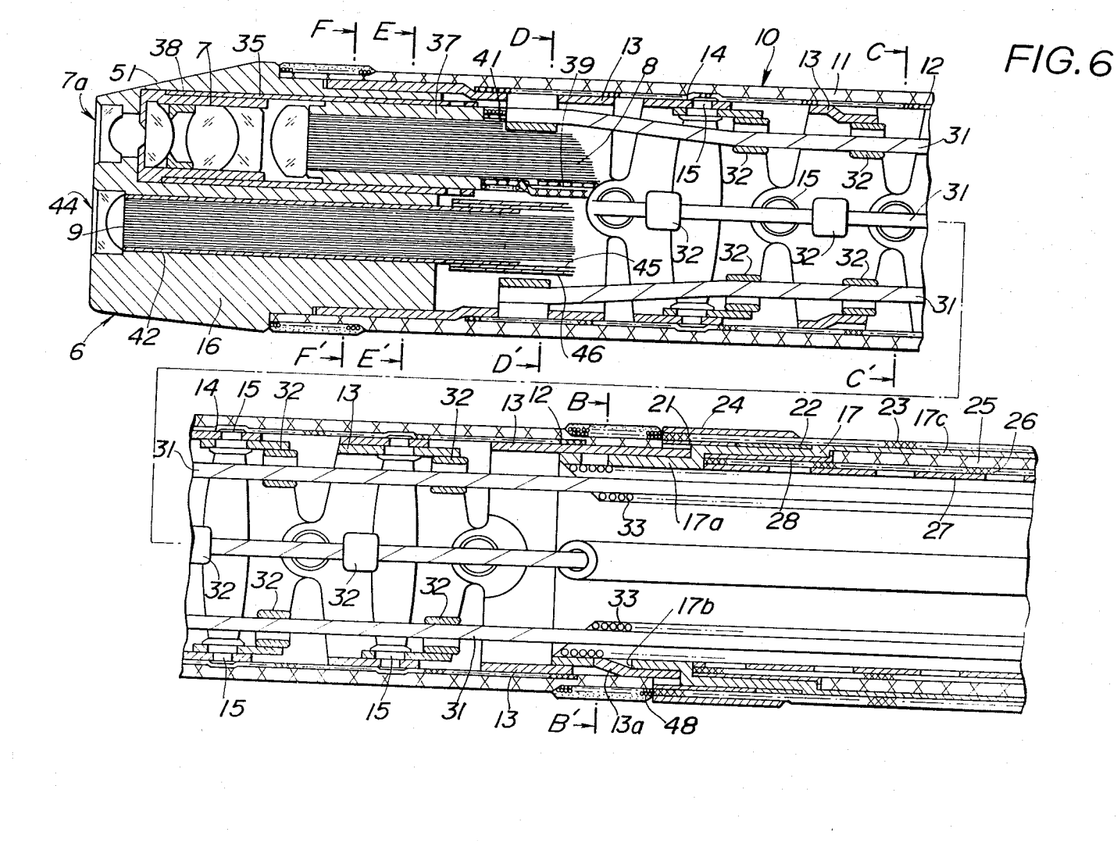
FIG. 6 is a sectional view of the endoscope tip of FIG. 3.

With reference to FIG. 6, the portion 10 of element 2 is comprised of a flexible tube 11 having a woven metal tube type inner lining 12 and a plurality of annular articulating rings 13 spaced axially along the interior thereof. With the exception of the endmost rings, each articulating ring 13 is pivotally connected to the adjacent connecting rings 13 by rivets 15 fitted to holes in connecting parts 14 projecting endwise from the periphery of each ring 13. Each such articulating ring 13 is provided with four projecting connecting parts 14 equally spaced around the circumference thereof. One pair of connecting parts 14 spaced 180° apart project in one axial direction and the other pair in the opposite axial direction. The assembly thus permitting each articulating ring 13, other than the endmost rings, to pivot about a first axis relative to the adjacent ring 13 connected by one pair of connecting parts 14 and to pivot about a second axis relative to the adjacent ring 13 connected by the other pair of connecting parts 14, with the second axis normal to the first axis. The connection of the articulating rings 13 is such as to permit vertical movement of the endoscope tip 6, as reviewed in FIG. 6 and movement normal to the plane of the FIG. 6 drawing.

Figure 10:
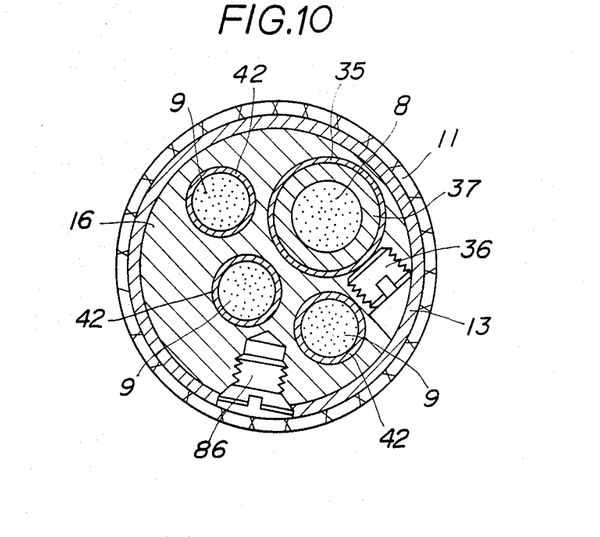
FIG. 10 is a sectional view taken along line E—E' in FIG. 6.

The forward endmost articulating ring 13 is fitted to a reduced diameter or stepped portion of the tip body 16 and secured by a machine screw 86 as shown by FIG. 10.

Figure 7:
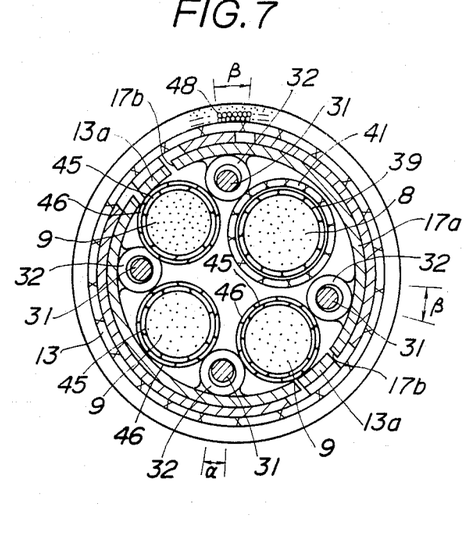
FIG. 7 is a sectional view taken along line B—B' in FIG. 6.

The rear endmost articulating ring 13 is externally fitted to a stepped or smaller diameter portion 17a at the forward end of a annular mouthpiece 17 and secured in place with a cement or other adhesive. To prevent forward movement of the rear endmost articulating ring 13 relative to the mouthpiece 17, cut-out slots 17b are provided to the mouthpiece 17 and locking pieces in the form of tabs 13a are provided in the overlying portion of the articulating ring 13. As shown by FIGS. 6 and 7, the tabs 13a are pressed into the slots 17b to secure the rear endmost articulating ring 13 against axial movement relative to the annular mouthpiece 17.

The elongate flexible tubular element 2 between the portion 10 and the central unit 3 is comprised of an outer woven metal sheath 23, an interior flexible tube lining 25, an inner, woven metal sheath 26 and an interior flexible spiral tube lining 27.

As shown by FIG. 6, the mouthpiece 17 is further stepped to provide a rearward extending cylindrical flange 17c. The forward end of the outer metal sheath 23 is secured at about the mid-point of the annular mouthpiece 17 by inner and outer fittings 21 and 24. An anti-rotational element 22 is also provided between the mouthpiece 17 and the interior surface of the metal sheath 23. The inner fitting 21 and the anti-rotational element 22 are provided with an interlocking, oppositley disposed tongues and grooves to prevent relative rotation when the fitting 21 engages the anti-rotational element 22 which in turn abuts the radial step on mouthpiece 17.

The outer periphery of the interior flexible tube lining 25 is fitted to the interior of the rearward extending cylindrical flange 17c. A ring 28 fitted to the outer peripheral surface at the forward end of the inner, woven metal sheath 26 is fitted internally of the mouthpiece 17. A flexible spiral tube 27 exerts pressure outwardly pressing the inner, woven metal sheath 26 and the interior flexible tube lining 25 against the cylindrical flange 17c.

The rear end of the tube 11 coating the woven metal sheath 12 is secured around the outer periphery of the rear endmost articulating ring 13 where it overlies the mouthpiece portion 17a. The rear end of the tube 11 is wound and compressed with several turns of thread as shown at 48. The winding 48 is fixed with a resin or adhesive. This facilitates easy replacement of the outer sheath 23 in the event of damage since the winding 48 can be unwound thereby providing access for removal of the outer fitting 24 and outer sheath 23.

The articulating rings 13 provided interiorly of the portion 10 of element 2 are longitudinally connected by four wires 31 which extend the full length of the elongate, flexible tubular element 2 from the tip 6 to the control unit 3.

Figure 9:
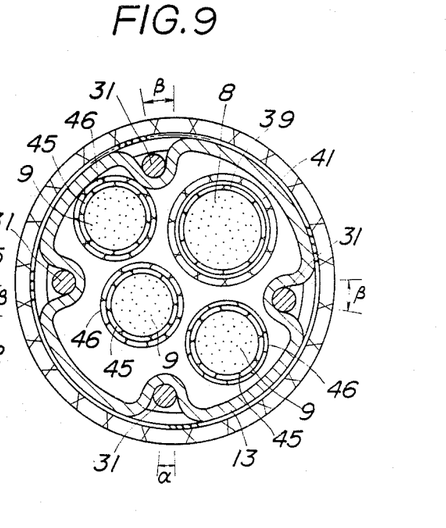
FIG. 9 is a sectional view taken along line D—D' in FIG. 6.

As shown by FIGS. 6 and 9, the forward end of each wire 31 is seated and secured in a radially inwardly depressed notch formed in the forward endmost articulating ring 13. The ends of the wires 31 may be brazed to the articulating ring 13 or, in the alternative, they may be fixed in a recess or through hole provided in the tip body 16.

The other ends of the wires 31 are connected to the knob 10A of control unit 3 which enables the operator to produce horizontal and vertical movement of the tip 6 as previously described.

Figure 8:
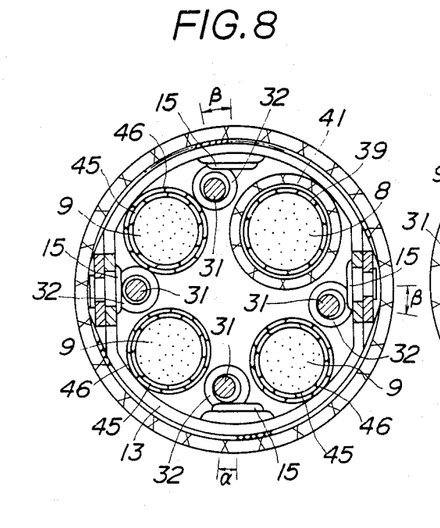
FIG. 8 is a sectional view taken along line C—C' in FIG. 6.

Between the control unit 3 and the portion 10 of the element 2 the four wires 31 are guided internally of four guide coils 33. The four wires 31 are guided internally of the articulating rings 13 by guide rings 32 fixed by brazing or the like to the inner peripheral surface of the articulating rings 13. As shown by FIGS. 6 and 8, the wires 31 pass through holes provided to guide rings 32 located closely adjacent the pivot points established by the rivets 15. By operating the control knob 10A to pull one wire 31 and relax the opposite wire of either pair of diametrically opposed wires 31, the forward endmost articulating ring 13 will pivot about one of the aforementioned axes and the remaining pivotally connected articulating rings will pivot in similar fashion thereby permitting the operator to selectively and remotely move the tip 6 to a desired location or orientation to illuminate and view an otherwise inaccessible object.

The angles d and B in FIGS. 7, 8 and 9 represent lag angles from the pivoting rivet positions in the vertical horizontal directions and are set respectively, for example, at 5 and 10 degrees. A lay angle of 0 degree is set for the rivet positions adjacent the wire 31 for which a lag angle is not indicated in the drawings.

The four wires 31 guided by the evenly spaced guide rings 32 and guide coils 33 divide the interior space of the pivotally connected articulating rings 13 and the spiral tube 27 into four sections. The image guide 8 and the three illuminating light guides 9 are each conveniently located in respective ones of the four sections.

The objective lens system 7 and the forward end of the image guide 8 are secured within a lens barrel 35 fitted to the interior of a stepped cylindrical bore through the tip body 16. The lens barrel is sealed with a hermetic seal and is secured to the tip body 16 with a machine screw 36 as shown by FIG. 10.

A front lens 7a of the objective lens system 7 is fixed in and serves as an observing window at the forward end of the bore through the tip body 16. The objective lens system 7 is assembled and secured in a frame 38 having a shoulder seated against the forward end of the lens barrel 35.

The forward end of the image guide 8 is fixed internally of a sleeve 37 which in turn is secured internally of the lens barrel 35.

Figure 11:
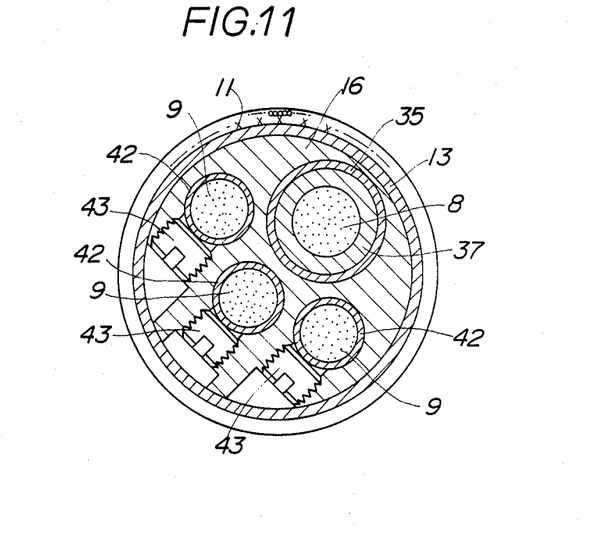
FIG. 11 is a sectional view taken along line F—F' in FIG. 6.

The portion of the image guide 8 that extends from the sleeve 37 rearward though the articulating rings 13 and the element 2 is coated with a thin walled tube 39 fitted to the rear end of the sleeve 37. An outer tube 41 is provided as a protective cover for the tube 39 and optical fibers therein. At its forward end, the tube 41 is wound tight against the internal components of the image guide with several turns of a thread and then fixed with an adhesive to the rear end of the sleeve 37. The forward ends of the three light guides 9 are each respectively fitted to and secured within one of three bores provided longitudinally of the tip body 16. The light guides 9 extend rearward through the articulating rings 3 and the element 2 to the control unit 3 where they are connected with the light guide cable 5. Internally of the articulating rings 13 and the element 2, the light guides 9 are coated with tubes 45 and 46. The tubes 45 and 46 are fitted and secured at their forward ends to the exterior surface of a sleeve 42 which is fitted and secured to the forward end of the bundle of optical fibers comprising the interior of the light guide 9. The sleeves 42 are fixed within the bores through tip body 16 by machine screws 43 as shown by FIG. 11. A light distributing lens is secured in the forward end of each through bore adjacent the forward end of each sleeve 42 to form illuminating windows 44.

Figure 4:
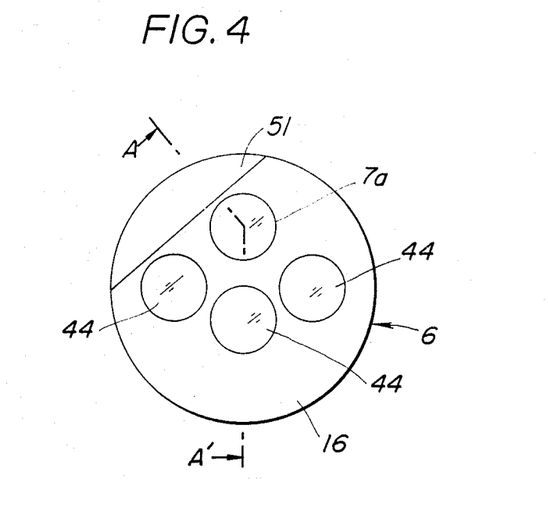
FIG. 4 is an end view of the endoscope tip of FIG. 3.
Figure 5:
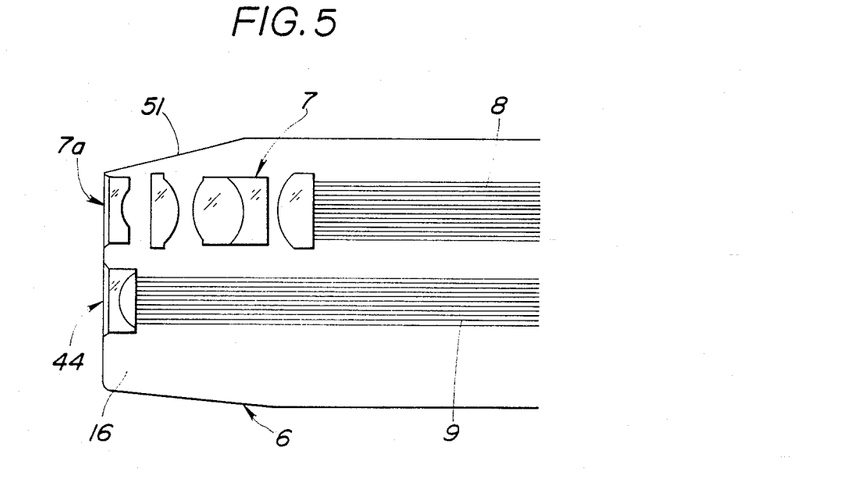
FIG. 5 is a view showing schematically the interior of the endoscope tip of FIG. 4, as though taken along the line A—A' of FIG. 4.

In the first embodiment of the invention, the body 16 of the tip part 6 of element 2 as shown by FIGS. 4, 5, 6 and 12 has been incised on the outer surface or cut away in an oblique direction not parallel with the longitudinal axis of the tip body 16 to form an inclined planar surface 51. The planar surface 51 is incised or cut away in such a manner that the greatest amount is removed at the forward end of the tip body 16. In this embodiment, as best shown by FIG. 4, a section of the tip body 16 is removed in such a manner that the forward edge of the inclined planar surface 51 is closely adjacent the observing window 7a and one of the illuminating windows 44.

Therefore, when using an endoscope having a tip body with an inclined planar surface such as the surface 51, one can press the surface 51 against the inner wall of a pipe or other cavity to be observed and the required observation can be made with a lower angle of incidence than with a conventional endocsope tip body not having such and inclined planar surface.

Figure 12:
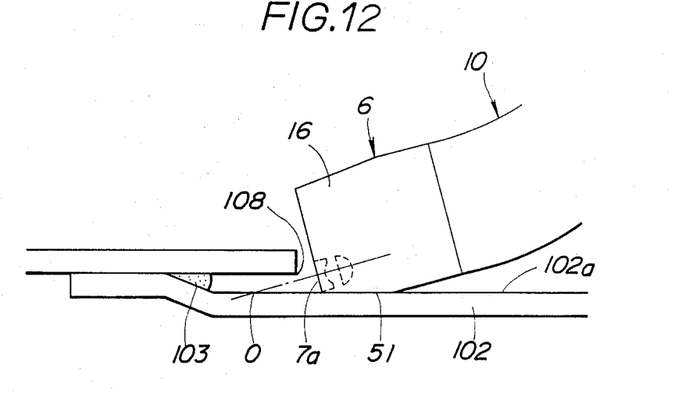
FIG. 12 is a view showing the tip of the endoscope of FIG. 3 in use.

FIG. 12 shows the use of an endoscope having a tip 6 in which the tip body 16 has been incised to provide an inclined planar surface 51 to inspect a relatively obscure welded joint 103 provided between a liner 102 and a projected edge part 108. The weldment 103 and the parts 102 and 108 are typical of the type of joint that may be provided internally of a combustion chamber within a jet engine. In this instance, when the portion 10 of the element 2 is manipulated by the operator to press the inclined planar surface 51 of the tip body 16 against the inner surface 102a of the liner 102, the angle of incidence is such that the optical axis 0 of the objective lens system will intersect the inner surface 102a of the liner well within the space between the part 108 and the liner 102 without interferenece by the part 108 as encountered in the FIG. 1 prior art example previously described. In this instance, the lower angle of incidence provided by the inclined planar surface 51 will enable the operator to illuminate and view the weldment 103 between the liner 102 and part 108.

In this embodiment, since the forward edge of the inclined planar surface 51 is closely adjacent both the observing window 7a and one of the illuminating windows 44 light from that illuminating window will be provided along substantially the same angle of incidence and will adequately illuminate objects observable through the observing window 7a.

FIG. 12 shows an end view of a tip comprising a second embodiment of the present invention. In FIG. 12, the incised surface 61 is formed by incising or cutting away the forward edge of the tip body 16 to provide an arcuate incised surface 61 of a radius of curvature larger than the radius of curvature of the outer circumference 6' of the tip body 16. The incised surface 61 in this second embodiment like the incised planar surface 51 of the first embodiment is cut away with the larger amount being removed from the forward end of the tip body 16 and the incised surface 61 tapering rearwardly to the outer circumference 6' of the tip body 16.

When observations are made with an endoscope tip having an arcuate incised surface such as the surface 61, the endoscope tip 6' can be moved more smoothly along the inner surface of an article such as the liner 102 of FIG. 12. Also, the tip 6' is more readily adjustable by rotation to center the image of the observed object in the visual field.

Figure 14:
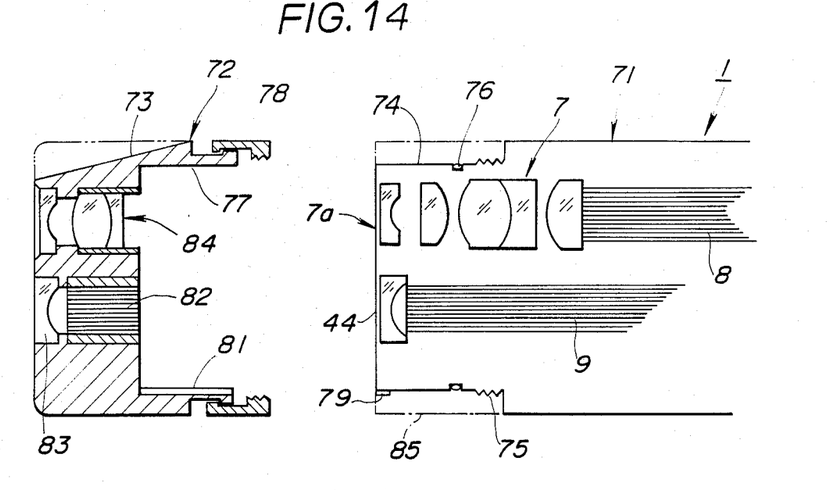
FIG. 14 is a view schematically showing the interior of an endoscope tip incorporating another embodiment of the present invention.

FIG. 14 shows a third embodiment of the present invention.

Figure 13:
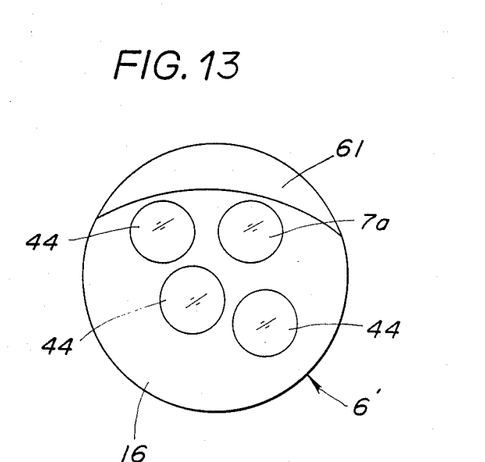
FIG. 13 is an end view showing a second embodiment of an endoscope tip according to the present invention.

In this embodiment, an incised surface 73 is provided on a tip adapter 72 which can be removably fitted to a tip body part 71 of an endoscope 1. The incised surface 73 may be an inclined planar surface similar to the surface 51 of the FIG. 4 embodiment or a curved surface similar to the surface 61 of FIG. 13.

The outer periphery of the tip body part 1 is machined at its forward end to provide a reduced diameter part 74 which is threaded as shown at 75. A peripheral groove is provided forward of the threaded section 75 and an O ring 76 is fitted in the groove.

The tip adapter 72 is recessed at 77 to fit snuggly over the reduced diameter portion 74 of tip part 71. A threaded ring 78 loosely fitted to the tip adapter 72 engages the threads 75 provided to the tip part 71 to secure the adapter 72. A groove 81 provided in the tip adapter recess 77 registers with and receives a projection 79 provided on the tip part 71 to prevent rotation of the tip adapter 72 relative to the tip part 71 and to ensure axial alignment of the optical elements provided in the tip adapter 72 and corresponding elements in the tip part 71. For example, the illuminating lens 83 and light guide 82 are axially aligned with the illuminating windows 44 in the tip part 71. Likewise, a vision angle varying lens 84 secured in a through hole provided to the tip adapter 82 is axially aligned opposite the observing window 7a in the tip part 71.

The tip adapter 72 may be used for varying the angle of vision or it may be fitted for observing a weldment or other object without varying the angle of vision through the incised 73.

In the event adapter 72 is not used with the tip part 71, a cap 85 such as that indicated by the phantom line in FIG. 14 may be fitted to the tip part 71. The cap 85 may itself be provided with an incised surface enhancing further use of the tip part 71.

Figure 15:
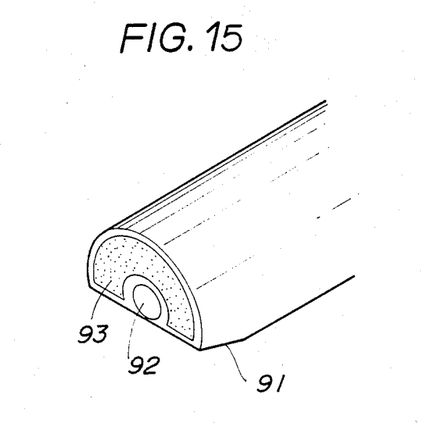
FIG. 15 is a perspective view showing an endoscope tip incorporating an additional embodiment of the present invention.

FIG. 15 shows a fourth embodiment of the present invention. In this embodiment, the forward edge of an incised surface 91 is provided adjacent an observing window containing an objective lens system and a arcuate illuminating window in the form of a circular band 93 is provided around the observing window 92 and adjacent the forward edge of the incised surface 91. With this embodiment, an object to be inspected can be brightly illuminated.

Figure 16:
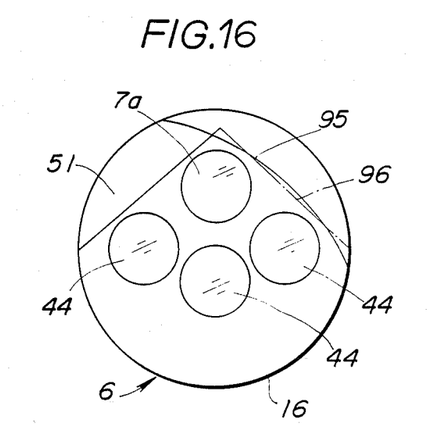
FIG. 16 is a perspective view showing an endoscope tip incorporating a further embodiment of the present invention.

FIG. 16 shows a fifth embodiment of the present invention. In this embodiment, a tip 6 of an endoscope is provided with two incised surfaces. One incised surface is a planar surface 51 similar to the inclined planar surface 51 of FIG. 4. In addition, a second incised surface 95 is formed to intersect the surface 51. The second incised surface 95 may be a convexly curved surface as indicated by the solid line in FIG. 16 or it may be a second inclined planar surface 96 as shown by the phantom line in FIG. 16. This embodiment is particularly well adapted to permit inspection of a corner or angular recess in a wall surface.

Although the endoscope 1 described in conjuction with the various embodiments of the present invention utilizes three illuminating windows, the present invention is not limited to that particular structure but may be used with endoscopes having optical systems of different structures.

As described above, according to the present invention, an incised surface is formed by incising or cutting the outer peripheral surface of an endoscope tip body in a direction inclined with the longitudinal axis of the tip body and thereby permitting a smaller angle of inclination of the axis of an objective lens system carried by said tip body when said incised surface is pressed against a surface or other part adjacent to an object to be viewed.

What is claimed is:

1. An endoscope tip body adpated for use at the insertable end of an elongated endoscope element adapted to be inserted into a pipe cavity or the like comprising;
   an illuminating optical system projecting an illuminating light out of an illuminating window formed on the end surface of said tip body;
   an objective optical system forming the image of an object through an observing window formed on the end surface of said tip body; and
   an incised surface formed by cutting a part of the outer surface of the tip body away to provide a tapered outer surface to said tip body with the forward edge of said tapered outer surface closely adjacent said observing window on the end surface of said tip body.

2. An endoscope tip body according to claim 1 wherein the forward edge of said tapered outer surface is closely adjacent to said illuminating optical system and said objective optical system.

3. An endoscope tip body according to claim 1 wherein a plurality of said illuminating optical systems are formed and one of them and said objective optical system are positioned closely adjacently to the forward edge of said incised, tapered surface.

4. An endoscope tip body according to claim 1 wherein said illuminating optical system is formed as a circular band to arcuately enclose said objective optical system and the ends of said band are adjacent to the forward edge of said incised surface.

5. An endoscope tip body according to any of claims 1, 2, 3 and 4 wherein said incised surface is an inclined planar surface.

6. An endoscope tip body according to any of claims 1, 2, 3 and 4 wherein said incised surface is a convexly curved surface.

7. An endoscope tip body according to claim 1, wherein said tip body includes two incised surfaces which intersect with each other and taper away from the end of the tip body in different directions.

8. An endoscope tip body part according to any of claims 1, 2, 3 or 4 wherein said incised surface is formed on an adaptor removably fitted to the outer periphery of said tip body.

9. An endoscope tip body according to claim 8 wherein said adaptor has an optical system for varying the angle of vision.

10. An endoscope tip part according to claim 9 wherein said adaptor has an illuminating optical system of light distributing characteristic set in response to said optical system for varying the angle of vision.

* * * * *